United States Patent [19]
Davis

[11] 4,123,344
[45] Oct. 31, 1978

[54] TWO FIRE CERAMIC SEALED OXYGEN SENSING DEVICE AND METHOD OF FORMING SAME

[75] Inventor: Donald C. Davis, Fostoria, Ohio

[73] Assignee: Bendix Autolite Corporation, Fostoria, Ohio

[21] Appl. No.: 787,721

[22] Filed: Apr. 15, 1977

[51] Int. Cl.² ............................................. G01N 27/46
[52] U.S. Cl. ........................... 204/195 S; 123/119 E; 264/61; 427/125
[58] Field of Search ............................ 204/15, 195 S

[56] References Cited

U.S. PATENT DOCUMENTS

| | | | |
|---|---|---|---|
| 2,486,871 | 11/1949 | Osterheld | 204/197 |
| 3,454,486 | 7/1969 | Davies | 204/195 S |
| 3,468,780 | 9/1969 | Fischer | 204/195 S |
| 3,616,407 | 10/1971 | Engell et al. | 204/195 S |
| 3,752,753 | 8/1973 | Fitterer | 204/195 S |
| 3,841,987 | 10/1974 | Friese et al. | 204/195 S |
| 3,847,778 | 11/1974 | Riddel | 204/15 |
| 3,940,327 | 2/1976 | Wagner et al. | 204/195 S |
| 3,960,692 | 6/1976 | Weyl et al. | 204/195 S |
| 4,040,930 | 8/1977 | Dillon | 204/195 S |

FOREIGN PATENT DOCUMENTS

2,307,451  8/1974  Fed. Rep. of Germany ....... 204/195 S

*Primary Examiner*—T. Tung
*Attorney, Agent, or Firm*—William G. Kratz, Jr.; Raymond J. Eifler

[57] ABSTRACT

A solid electrolyte oxygen sensing device, and a method for making the same, wherein an electrolyte wafer is sealed within a ceramic insulator by the shrinkage of the ceramic insulator when it is fired. The wafer is formed from an electrolytic material and is fired. The vitrified wafer is placed in a recess in the unfired ceramic insulator and the insulator is then fired, with the resulting shrinkage of the insulator material sealing the wafer in place.

1 Claim, 1 Drawing Figure

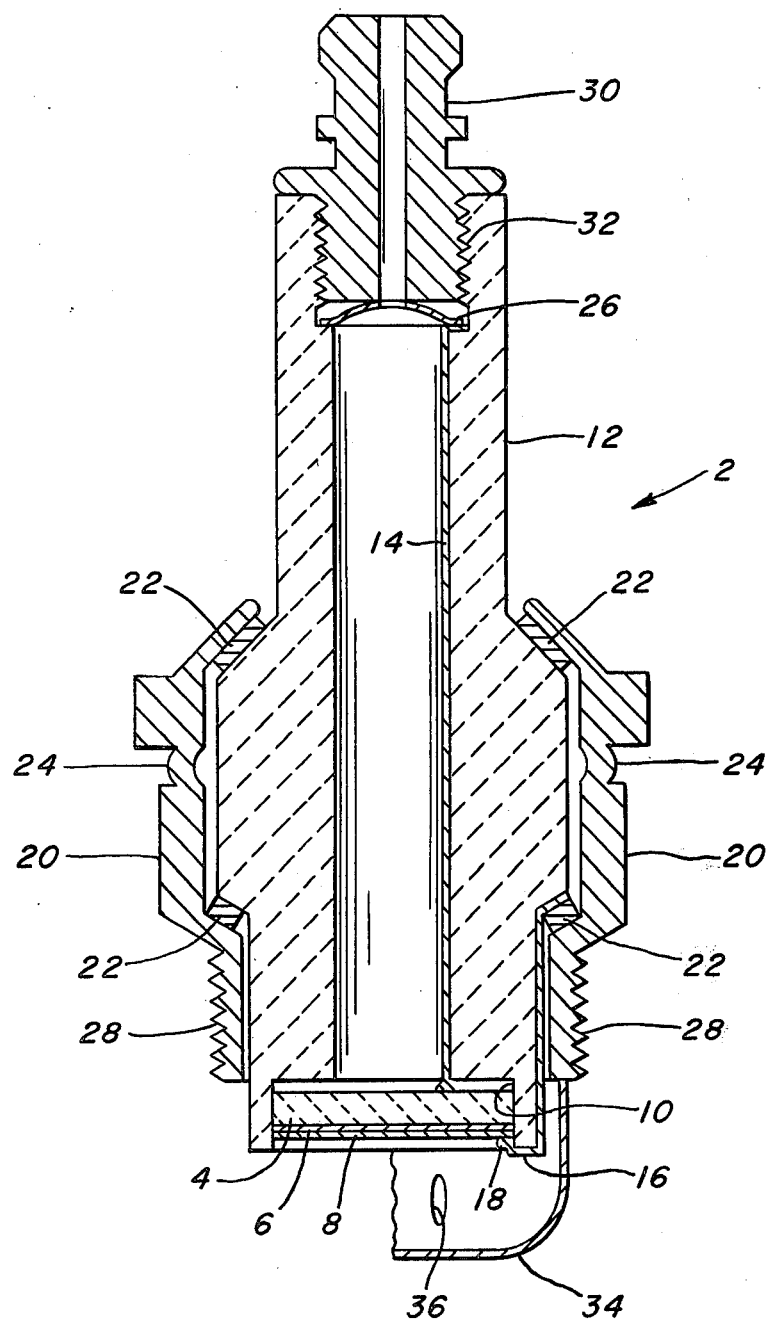

TWO FIRE CERAMIC SEALED OXYGEN SENSING DEVICE AND METHOD OF FORMING SAME

BACKGROUND OF THE INVENTION

1. Field of the Invention

The present invention relates generally to oxygen sensing devices and more particularly to such devices utilizing an electrolytic wafer and intended for use in the exhaust path of an internal combustion engine.

2. Prior Art

In recent years, it has become known to measure the content of oxygen in combustion gases by the use of an electrochemical oxygen sensing device which is exposed to the exhaust gases in an internal combustion engine. The prior art devices have been of two general types, the first of these being referred to as the thimble type, examples of which are disclosed in U.S. Pat. Nos. 3,960,693 and 3,978,006; and the second of these being known as a disc or wafer type, examples of which are shown in U.S. Pat. Nos. 3,909,385 and 3,940,327. Sensors of both types utilize a solid electrolyte such as zirconium oxide ($ZrO_2$) which generates a voltage between the electrodes of the sensor when there is a difference in oxygen partial pressures between the exhaust gas side of the electrolyte and the reference, or air, side of the electrolyte. Because of this, it is absolutely necessary to maintain a good seal along the edges of the electrolyte so that the exhaust gas and reference gas are kept separated. The required seal has been accomplished in prior art devices in various ways. In U.S. Pat. No. 3,909,385, a wafer of electrolyte material is sealed in a metal housing by a hermetic seal formed from a metal oxide frit which wets both the surface of the wafer and the pre-oxidized metal housing. Upon heating, the frit softens to form the necessary seal. In U.S. Pat. No. 3,940,327, means for holding an electrolyte wafer in contact with the flange of a metallic housing is described wherein a ceramic insulating sleeve is used in connection with a high temperature fiber gasket to provide a hermetic seal to prevent leakage of exhaust gases around the wafer. The principal seal is thus provided by the high temperature ceramic fiber gasket.

The present invention is intended to provide an improved and alternate method of forming a gas-tight seal in an oxygen sensing device of the type mentioned.

SUMMARY OF THE INVENTION

The present invention provides an alternative approach to the formation of a gas-tight seal in mounting an electrolyte wafer to its insulator in an oxygen sensing device. The invention provides for a device which does not require gaskets or external sealing devices of metal or other materials.

The invention is an oxygen sensing device characterized by an electrolyte wafer 4 formed from a quadrivalent oxide ceramic composition and vitrified by firing. An insulator 12 is formed from a ceramic composition that has a coefficient of thermal expansion which is compatible with that of the wafer 4 but which matures or vitrifies at a lower firing temperature. A counterbored recess 10 is formed within the insulator and the vitrified wafer 4 is placed into the recess 10 of the unfired insulator 12 subsequent to which the insulator 12 is fired. The firing of the insulator 12 results in shrinkage of the insultor material which seals the wafer 4 within the recess 10.

In one embodiment of the invention, the method for making the oxygen sensing device comprises forming a wafer 4 from an electrolytic ceramic material, vitrifying the wafer 4 by firing it at a predetermined elevated temperature, forming an elongated hollow insulator 12 having a counterbored recess 10 in one end thereof from a ceramic composition which has a coefficient of thermal expansion which is compatible with the coefficient of thermal expansion of the ceramic material of the wafer 4, and which vitrifies at a lower temperature than the firing temperature of the wafer 4, placing the wafer 4 in the counterbored recess 10 of the insulator 12, firing the insulator 12 at a temperature which is lower than the firing temperature of the wafer 4 such that the insulator 12 shrinks and seals the wafer 4 within the recess 10 in the insulator 12. After the seal is formed, the sensor is completed by coating the outer side of the wafer with an electrode 6, securing an electrode 14 to the inner side of the wafer and another electrode 16 to the electrode 6, such as at 18, on the outer side of the wafer 4 and securing a metal shell 20 around a portion of the insulator 12 intermediate the ends thereof. A top terminal 30 is secured to the top of the insulator 12 such that it is in electrical contact with the inner electrode 14.

BRIEF DESCRIPTION OF THE DRAWING

The FIGURE is a sectional elevation view of the oxygen device of the present invention taken along a plane passing through the axis of the device.

DETAILED DESCRIPTION OF THE PREFERRED EMBODIMENT

The oxygen sensing device of the present invention designated generally as 2 can best be described with reference to the accompanying drawing. A wafer or disc 4 is formed from a solid quadrivalent oxide ceramic composition, such as zirconium dioxide ($ZrO_2$) or ceric dioxide ($CeO_2$), each of which is doped with an appropriate quadrivalent oxide, such as gadolinium oxide ($Gd_2O_3$) or yttrium oxide ($Y_2O_3$), or a divalent oxide, such as magnesium oxide (MgO), or calcium oxide (CaO). The wafer is vitrified by firing at a temperature which is determined by the material used but which is, for example, for a $ZrO_2$ wafer approximately 2950° F.

A hollow elongated insulator 12 is formed from a ceramic composition such as spinel, mullite, aluminum oxide or cordierite or similar material which has a coefficient of thermal expansion which is compatible with the coefficient of thermal expansion of the wafer 4, but which vitrifies at a firing temperature which is 200° F. or more, preferably 200°–500° F., lower than the firing temperature of the wafer 4. For example, with a zirconium dioxide composition wafer, the vitrification temperature of the insulator ceramic composition should be about 2750° F. or lower. Also, in the use of a zirconium dioxide composition wafer, the coefficient of thermal expansion would be about $8.0 \times 10^{-6}$ inches/inch/° C., and the ceramic composition used in the insulator should be such that the coefficient of thermal expansion of the insulator material would be between 7.5 to 8.5 $\times$ $10^{-6}$ inches/inch/° C., or about plus or minus a half unit range. Such a coefficient of thermal expansion for a particular ceramic insulator may be adjusted, as is known, by use of various fluxes and compositions. The insulator 12 is formed with a counterbored recess 10 which is an extension of the hollow center of the insulator 12. The previously fired wafer 4 is placed into the counterbore recess 10 of the unfired ceramic insulator 12. The insulator 12 is then fired to maturity, or vitrified at a temperature of 200° F. or more lower than the wafer vitrification temperature, during which firing there is a densification and shrinkage of the insulator 12 which seals the wafer 4 in situ and closes off the lower end of the hollow interior of the insulator 12 with one side of the wafer facing the interior of the insulator and the other side facing the exterior of the insulator.

Subsequent to the firing of the insulator 12, a porous platinum electrode 6 is applied to the exterior surface of the wafer 4 by prior art methods of vapor deposition, or painting or the like. A porous protective coating 8 of a material such as spinel or mullite may be plasma or flame sprayed onto the exterior surface of the wafer 4 over the platinum electrode 6 to protect the electrode 6 and the wafer 4 from abrasive exhaust products. A platinum interior electrode 14 is then painted or otherwise fixed to the insulator and fired on the interior of the insulator 12, in contact with the interior side of the wafer, while a platinum exterior electrode 16 is painted, or otherwise fixed, and fired on the external surface of the insulator 12. The interior platinum electrode 14 extends upward through the interior of the insulator 12 to a threaded recess 32. A disc contact spring 26 is placed within the threaded recess 32 in contact with the electrode 14 and a vented top terminal 30 is threaded into the threaded recess 32 of the insulator 12 completing the inner electrode circuit.

The insulator 12, with the wafer 4 in place, is then placed into a steel shell 20 having exterior threads 28. Nickle gaskets 22 are placed between the steel shell 20 and the insulator 12 to form a seal between the steel shell 20 and the insulator 12. The steel shell 20 is next pressure-crimped into place with a hydraulic press and die by applying high current and pressure which results in resistance heating and collapsing of the reduced hot press area 24 of the steel shell 20. Subsequent cooling of the unit to ambient temperature results in a hermetic seal by the nickle gaskets 22. Contact between the exterior platinum electrode 16, the nickle gaskets 22 and the steel shell 20 results in the completion of the exterior electrode circuit.

If desired, a metallic shield 34, such as of stainless steel, having apertures 36 therein may be fixed to the sensor unit to protect the electrolyte wafer from direct impingement by hot, fast flowing gases.

There has been described an oxygen sensing device and method of assembly which eliminates mechanical seals and the possible failure of such seals. Fewer parts are required in the manufacture of the device of the present invention which reduces the possibility of mechanical failure. The insulator 12 extends from the top of the shell 20 which greatly reduces the possibility of the unit being shorted out by road splash. The sensor of the present invention is therefor less expensive to manufacture and more reliable in operation.

I claim:
1. An oxygen sensing device comprising:
    a hollow, elongated, ceramic insulating tube having first and second open ends, said first end having a recess formed therein coaxial with the tube;
    a wafer formed of a solid electrolyte ceramic material positioned in said recess and secured therein by direct engagement with walls of said recess to provide an inner surface of the wafer facing the interior of the hollow tube and an outer surface of the wafer facing away from the hollow tube;
    first conductive means along the inside of the tube in contact with the inner surface of the wafer;
    a threaded recess in said second end of the insulating tube;
    a threaded hollow conductive means positioned in the threaded recess, and engaged with said insulating tube, in conductive contact with said first conductive means;
    second conductive means along the outside of the tube in contact with the outer surface of the wafer; and
    a metal shell intermediate the ends of the insulating tube and enclosing a portion of the same, said shell being in contact with the second conductive means.

* * * * *